(12) United States Patent
Chen et al.

(10) Patent No.: US 9,126,968 B2
(45) Date of Patent: Sep. 8, 2015

(54) QUINIC ACID DERIVATIVE, PROCESS FOR PREPARATION AND USES THEREOF

(71) Applicant: NATIONAL APPLIED RESEARCH LABORATORIES, Taipei (TW)

(72) Inventors: Hueih-Min Chen, Hsinchu (TW);
Chung-Ming Sun, Hsinchu (TW);
Chih-Yu Huang, Hsinchu (TW)

(73) Assignee: National Applied Research Laboratories, Taipei (TW)

( * ) Notice: Subject to any disclaimer, the term of this patent is extended or adjusted under 35 U.S.C. 154(b) by 0 days.

(21) Appl. No.: 13/916,665

(22) Filed: Jun. 13, 2013

(65) Prior Publication Data

US 2014/0371445 A1     Dec. 18, 2014

(51) Int. Cl.
*C07D 317/72*     (2006.01)

(52) U.S. Cl.
CPC .................. *C07D 317/72* (2013.01)

(58) Field of Classification Search
CPC .................................................... C07D 317/72
USPC ....................................................... 549/332
See application file for complete search history.

(56) References Cited

U.S. PATENT DOCUMENTS

| | | | |
|---|---|---|---|
| 2010/0132504 A1* | 6/2010 | Miller et al. | ................. 74/606 A |
| 2010/0144828 A1* | 6/2010 | Wu et al. | .................... 514/423 |

FOREIGN PATENT DOCUMENTS

WO     WO 2010/132504     * 11/2010

OTHER PUBLICATIONS

Phoon et al, J. of Combinatorial Chemistry, 1999, 1(6), 484-492.*

* cited by examiner

*Primary Examiner* — Shailendra Kumar
(74) *Attorney, Agent, or Firm* — Rosenberg, Klein & Lee

(57) ABSTRACT

The present invention relates to a quinic acid derivative, preparation process of the same and pharmaceutical uses thereof. The quinic acid derivative has a quinic acid-like structure which binds to CD28, blocks T-cell signal 2 pathway via CD28, and suppresses T-cell activation. The C-1 carboxyl group, the C-3 hydroxyl group and the C-4 hydroxyl group of quinic acid are modified to attenuate the cytotoxicity of the quinic acid derivative. The preparation process of the quinic acid derivative comprises 2 steps of: treating quinic acid with the first reagent in the presence of the acid catalyst to form an immediate; and treating the immediate with the second reagent to from the quinic acid derivative. With the ability to suppress T-cell activation, the quinic acid derivative is used to treats an autoimmune disease, an allergy, transplant rejection or other related immune disorder.

5 Claims, 11 Drawing Sheets

| No. | R1 | R2 | No. | R1 | R2 |
|---|---|---|---|---|---|
| 1315 | -CH₂-phenyl | =C(CH₃)₂ | 1321 | -CH-cyclopentyl | =C(CH₃)₂ |
| 1316 | -CH₂CH(CH₃)₂ | =C(CH₃)₂ | 1322 | -CH₂CH₂-morpholinyl | =C(CH₃)₂ |
| 1317 | -CH₂CH₂OCH₃ | =C(CH₃)₂ | 1323 | -CH₂CH₂CH₂CH₃ | =C(CH₃)₂ |
| 1318 | -CH₂CH₂CH₃ | =C(CH₃)₂ | 1324 | -CH₂CH(CH₃)₂ | =cyclohexyl |
| 1319 | -CH₂CH(CH₃)₂ | =C(CH₃)₂ | 1325 | -CH₂CH(phenyl)₂ | =C(CH₃)₂ |
| 1320 | -CH₂-cyclohexenyl | =C(CH₃)₂ | 1326 | -CH₂-(2-pyridyl) | =cyclohexyl |

| No. | Yields of quinic acid derivative | No. | Yields of quinic acid derivative |
|---|---|---|---|
| 1315 | 76% | 1321 | 87% |
| 1316 | 91% | 1322 | 68% |
| 1317 | 86% | 1323 | 92% |
| 1318 | 92% | 1324 | 93% |
| 1319 | 81% | 1325 | 90% |
| 1320 | 88% | 1326 | 72% |

Fig 4

QUINIC ACID DERIVATIVE, PROCESS FOR PREPARATION AND USES THEREOF

BACKGROUND OF THE INVENTION

1. Fields of the Invention

The present invention relates to a quinic acid derivative, particularly to a cynarin-analogous quinic acid derivative which binds to CD28, preparation process of the same from a quinic acid and pharmaceutical uses via suppressing T-cell activation thereof.

2. Descriptions of Related Art

T-cells play a pivotal role in the initiation and regulation of immune responses to antigens. The activation of T-cells is tightly controlled by many positive and negative regulatory processes to prevent pathologically over-active or under-active immune responses. Optimal T-cell activation requires both signal 1 and signal 2 pathways while T-cells are stimulated by specific external stimuli. Antigen-presenting cells (APCs) such as dendritic cells express major histocompatibility complex (MHC) molecules on their cell surfaces and present antigen fragments with the MHC molecules. The signal 1 pathway is initiated by a binding interaction between the T-cell receptor (TCR) of T-cells and the antigen-MHC complex of APCs. The signal 2 is induced by a binding between a co-stimulatory molecule such as CD80 (also known as B7-1) or CD86 (also known as B7-2) of APCs and CD28 of T-cells, providing a co-stimulatory pathway. TCR engagement in the absence of the signal 2 leads to T-cell anergy which is a hyporesponsive state of T-cells.

The complete immune activation of T-cells is not desirable in response to self-antigens or allergens. The over-activations of T-cells against self-antigens or allergens cause autoimmune diseases or allergic conditions. Thus, declining the signal 2 pathway to promote T-cell anergy represents a strategy for the treatment of an autoimmune disease or an allergy. Because of the overlapping among intercellular signal transduction pathways, interfering signal pathways inside cell may cause a sever side effect (e.g., both signal 1 and signal 2 are simultaneously blocked). Thus, blocking signal pathways (e.g., either signal 1 or signal 2 can only be blocked) from outside provides a milder way to suppress signal transduction. For example, a non-mitogenic anti-CD28 antibody can be considered as a T-cell blocker to block the signal 2 pathway outside the T-cell. However, due to the fragile nature and the poor stability of antibodies, using them as drugs has many drawbacks. Acid and luminal proteases in the gastrointestinal tract limit oral availability of antibodies, and antibodies loss their 3D structures and functions easily. Otherwise, immune responses may be induced by antibody drugs and therefore lower the therapeutic utility of antibody drugs.

Using small compounds which mimic metabolites as drugs to block target pathways can overcome the drawbacks described above. To develop an ideal T-cell blocker, the inventor establishes a screening method named "after flowing through immobilized receptor (AFTIR) method" which refers to Taiwanese patent publication no. 1355493 and uses it to isolate a targeting component which specifically binds to CD28 from western purple coneflower (*Echinacea purpurea*) extracts. The targeting component is identified as cynarin, which having the formula as shown in FIG. 1. Due to the cytotoxicity of cynarin, the inventor delivers a cynarin analogue which is effective to block CD28 but less cytotoxic than cynarin. The inventor finds out that the key blocking factor (KBF) of cynarin binding to CD28 is a quinic acid-like section by molecular dynamic simulating 3D structures of cynarin and CD28. Thus, the inventor derives a cynarin-analogous quinic acid derivative with modifications for attenuating the cytotoxicity.

Accordingly, the present invention provides a cynarin-analogous quinic acid derivative, process for preparation the same from a quinic acid and pharmaceutical uses via suppressing CD28-dependent T-cell activation thereof. According to the present invention, the drawbacks according to the prior art such as anti-CD28 antibodies or cynarin as described above can be improved; the oral stability can be increased; and the cytotoxicity can be attenuated.

SUMMARY OF THE INVENTION

An objective of the present invention is to provide a quinic acid derivative, which has a quinic acid-like structure for binding to CD28 and blocking CD28-dependent T-cell activation.

Another objective of the present invention is to provide a process for preparation of the quinic acid derivative, which forms a lactone immediate in the presence of acid catalyst at first and treats the lactone immediate with an amine reagent to generate the quinic acid derivative product under microwave irradiation.

Still another objective of the present invention is to provide uses of the quinic acid derivative, which treats autoimmune diseases, allergies or transplant rejections by suppressing the T cell activation via blocking CD28.

In order to achieve the above objects, a cynarin-analogous quinic acid derivative, process for preparing the same, and uses of the same are provided. The quinic acid derivative comprises a quinic acid-like structure, which is the KBF of cynarin for binding to and blocking CD28 and suppressing T-cell activation.

Furthermore, the chemical formula of the quinic acid derivative is:

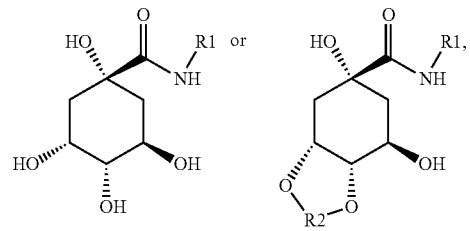

wherein R1 is an organic functional group, and R2 is a hydroxyl-protecting group.

The ability of the quinic acid derivative to block CD28 is due to the structure from quinic acid while the key blocking factor of cynarin which binds to the specific binding site of CD28 is a quinic acid-like structure. Otherwise, the cytotoxicity of the quinic acid derivative is reduced while the C-1 carboxyl group of quinic acid is modified by amino group of a second reagent and forms a peptide bond (e.g., —C(O)OH is replaced by —C(O)NHR1). Additionally, more stable quinic acid derivative is formed if a first reagent is added and forms a hydroxyl-protecting group to protect the C-3 hydroxyl group or the C-4 hydroxyl group of quinic acid. Because the C-3 hydroxyl group is cis to the C-4 hydroxyl group, these two hydroxyl groups can react with one molecule (second reagent) which forms one hydroxyl-protecting group to protect both of the C-3 and C-4 hydroxyl groups.

The process of preparing the quinic acid derivative from a quinic acid comprises two steps: First, treats a quinic acid with a strong acid and a first reagent (R2=O) to generate an intermediate having the chemical formula:

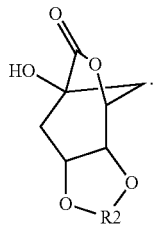

Next, treats the intermediate with a second reagent (R1-NH$_2$) to generate the quinic acid derivative as described above. The process proceeding under microwave irradiation and 100° C. promotes the reaction rate and shortens the time required to only 5 minutes.

The use of the quinic acid derivative is suppressing the T cell activation by binding to CD28 and blocking CD28-dependent signal 2 pathway, thus the quinic acid derivative can be used in pharmaceutical treatment of autoimmune diseases, allergies or transplant rejections therefore.

BRIEF DESCRIPTION OF THE DRAWINGS

FIG. 4 shows the yields of a series of quinic acid derivatives;

DETAILED DESCRIPTION OF THE PREFERRED EMBODIMENT

In order to make the chemical structure and characteristics as well as the effectiveness of the present invention to be further understood and recognized, the detailed description of the present invention is provided as follows along with embodiments and accompanying figures.

Figure 1:
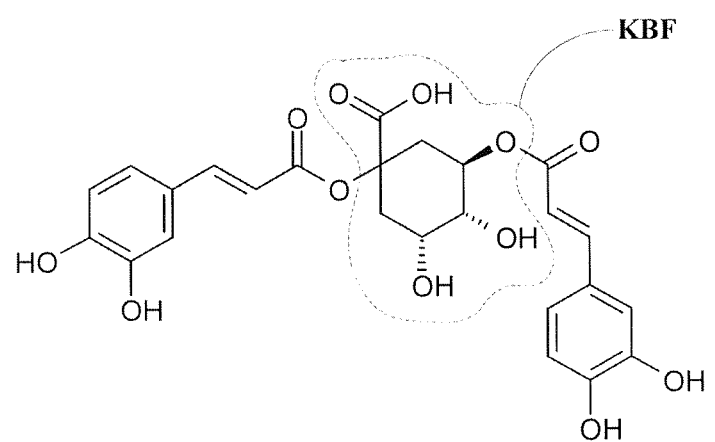
FIG. 1 shows the chemical structure of quinic acid.
Figure 2:
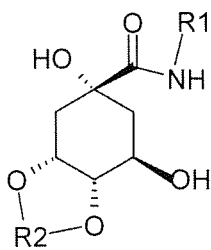
FIG. 2 shows the chemical structures of a series of quinic acid derivatives with various R1 and R2.
Figure 3:
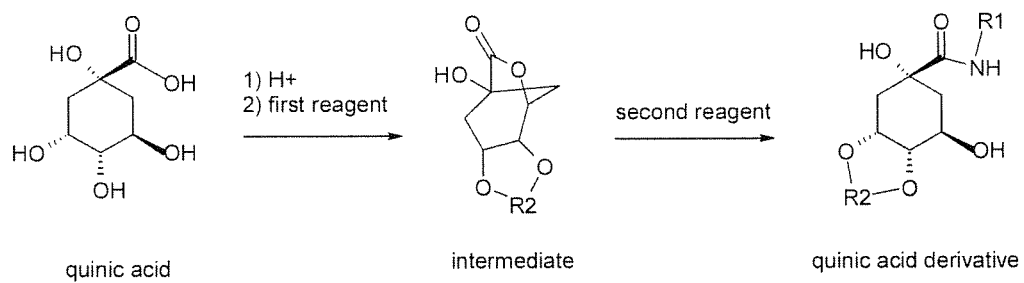
FIG. 3 shows the synthetic processes of a series of quinic acid derivatives with various first and second reagents.

Please refer to FIG. 2, which shows a series of quinic acid derivatives according to the present invention, and all of them are numbered and have the formula:

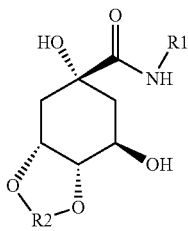

wherein R1 is an organic functional group, and R2 is a hydroxyl-protecting group. As mentioned before, the C-3 hydroxyl group of quinic acid (as shown in FIG. 3) is cis and adjacent to the C-4 hydroxyl group, thus they are able to bond to one R2. As shown in FIG. 2, R2 is a hydroxyl-protecting group which bonds to the two oxygen atoms of C-3 hydroxyl group and C-4 hydroxyl group and releases one water molecule, protecting both C-3 hydroxyl group and C-4 hydroxyl group. Both the peptide bond (R1NH—C(O)) and the hydroxyl-protecting group attached to the two oxygen atoms (O—R2-0) protect the quinic acid derivative from hydrolysis and prevent the releasing of cytotoxic quinic acid therefore.

Refer to FIG. 3, which shows the synthesis process of a series of quinic acid derivatives according to the present invention. As shown in FIG. 3, the synthesis process comprises 2 steps of:

Step 1: treating a quinic acid with an strong acid and a first reagent to generate the intermediate; and Step 2: treating the intermediate with a second reagent to generate the quinic acid derivative.

In the step 1, a strong acid such as sulfuric acid is added to catalyze the lactonization or the ketalization of the quinic acid. In presence of the acid catalyst, the oxygen atom of C-5 hydroxyl group nucleophilically attacks the C-1 carbonyl group and generates a five membered lactone ring of the intermediate. In presence of both the ketone first reagent which has a carbonyl group and the acid catalyst, the oxygen atoms of C-3 and C-4 hydroxyl groups also nucleophilically attack the carbonyl carbon of the first reagent successively and thus form five membered ketal ring of the lactone intermediate. The ketal structure protects both C-3 and C-4 hydroxyl groups. Otherwise, The step 1 is less time-consuming when it proceeds at high temperature such as 100° C. than at room temperature. Furthermore, the step 1 processes faster under microwave irradiation. For example, when quinic acid reacts with acetone as the first reagent, it requires 12 hours for yielding 85% of the lactone intermediate. However, while the same reaction is performed under microwave irradiation (100° C.), it yields 98% of the lactone intermediate within 5 minutes.

In the step 2, the lactone intermediate reacts with the amine second reagent having the formula R1-NH$_2$ and generates the quinic acid derivative. The nitrogen atom of amino group nucleophilically attacks the carbonyl group of the lactone intermediate, lead to the release the lactone ring strain formed in the step 1 and the formation of the peptide bond, yielding an amide (the quinic acid derivative) and a free water in the product. Under microwave irradiation (100° C.), the reaction proceeds for 5 minutes in very good yields. The yields of the series of quinic acid derivatives according to the present invention are shown as FIG. 4.

Figure 5:
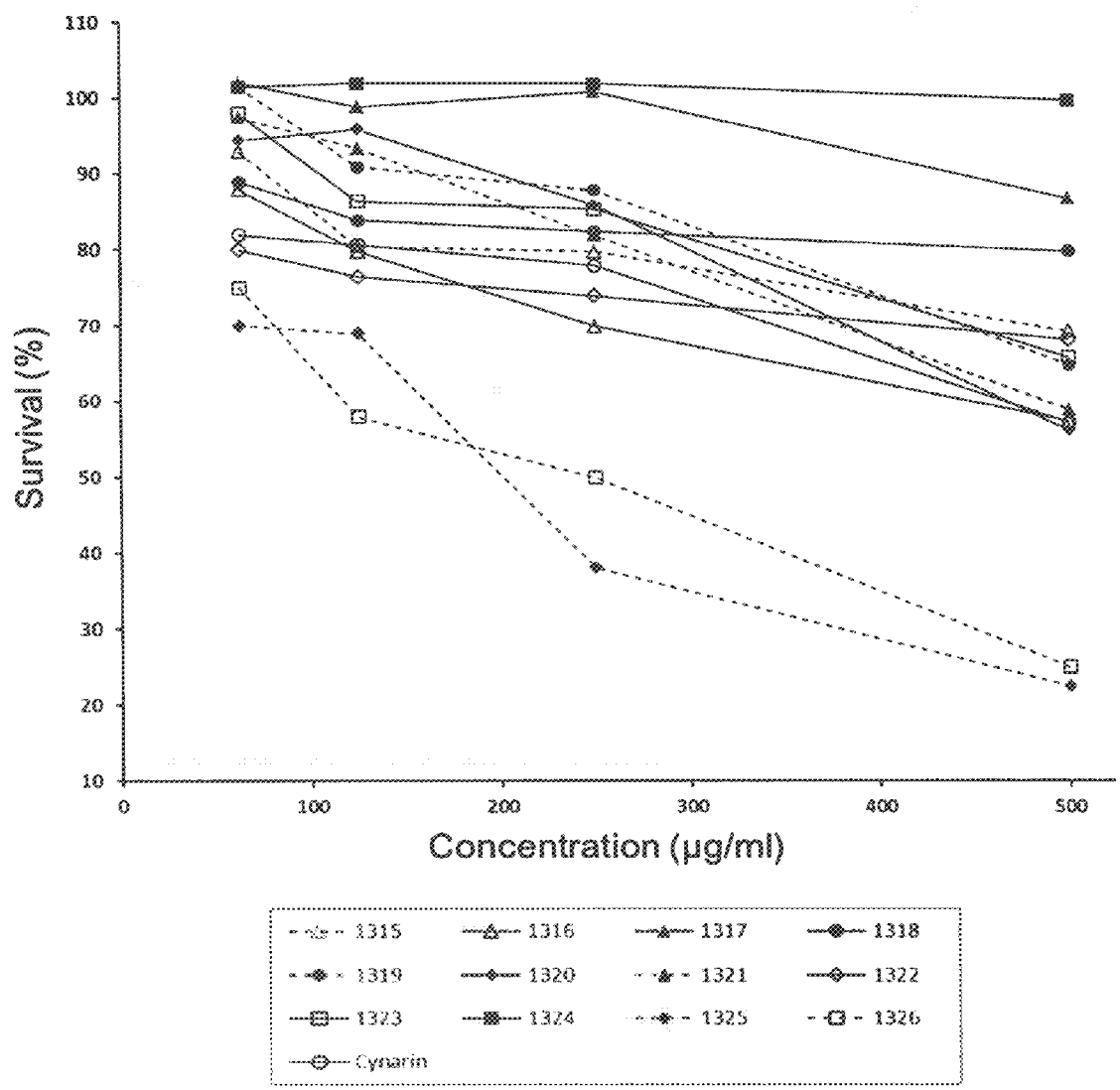
FIG. 5 shows the results of an in vitro cytotoxicity test of a series of quinic acid derivatives.

Refer to FIG. 5, which shows the results of an in vitro cytotoxicity test of a series of quinic acid derivatives while the survival rates of T-cells versus the concentration of cynarin and quinic acid derivatives are plotted. The amount of survival T-cells is measured by MTT assay. As shown in FIG. 5, the cell survival rates of the quinic acid derivatives numbered 1315, 1316, 1317, 1318, 1319, 1320, 1321, 1322, 1323 and 1324 is higher than cynarin. Conversely, they are less cytotoxic than cynarin.

Figure 6:
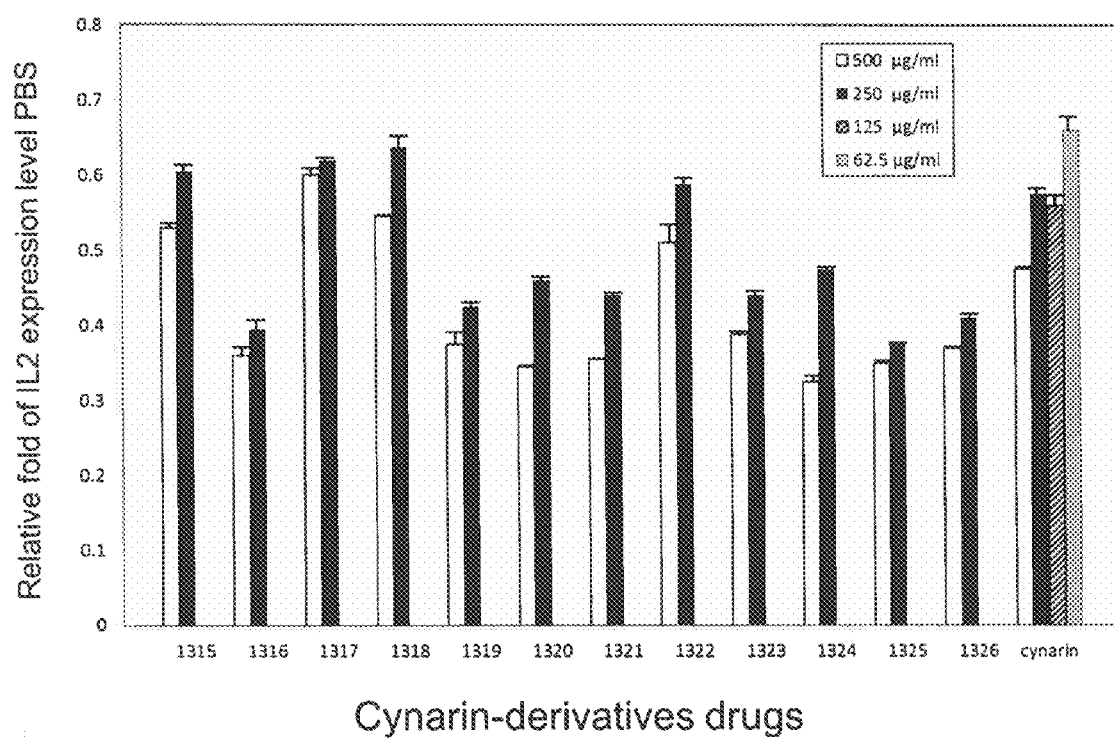
FIG. 6 shows the results of an in vitro efficacy test of a series of quinic acid derivatives.

Refer to FIG. 6, which shows the results of an in vitro efficacy test of a series of quinic acid derivatives while the productions of IL-2 from T-cells versus various concentrations of cynarin and the quinic acid derivatives are presented. The production of IL-2 is reduced when the activation of T-cells is interfered. As shown in FIG. 6, the quinic acid derivatives numbered 1316, 1319, 1320, 1321, 1323, 1324, 1325 and 1326 present higher (or equal) efficacy to suppress T-cell activation as compared with cynarin.

Due to the lowest cytotoxicity and high efficacy of the quinic acid derivative which is numbered 1324 (represented as Cyn-1324 below), the inventor performs further experiments to test effectiveness of Cyn-1324. The chemical structure formula of Cyn-1324 is:

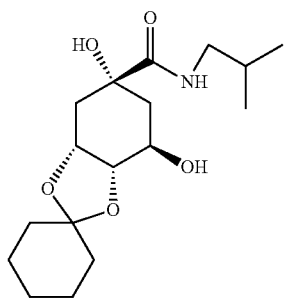 [SMILES: CC(C)CNC(=O)[C@@]1(O)C[C@@H](O)[C@@H]2OC3(CCCCC3)O[C@@H]2C1]

and named (3aR,5R,7R,7aS)-5,7-dihydroxy-N-(2-methylpropyl)hexahydrospiro[1,3-benzodioxole-2,1'-cyclohexane]-5-carboxamide by IUPAC nomenclature.

Figure 7:
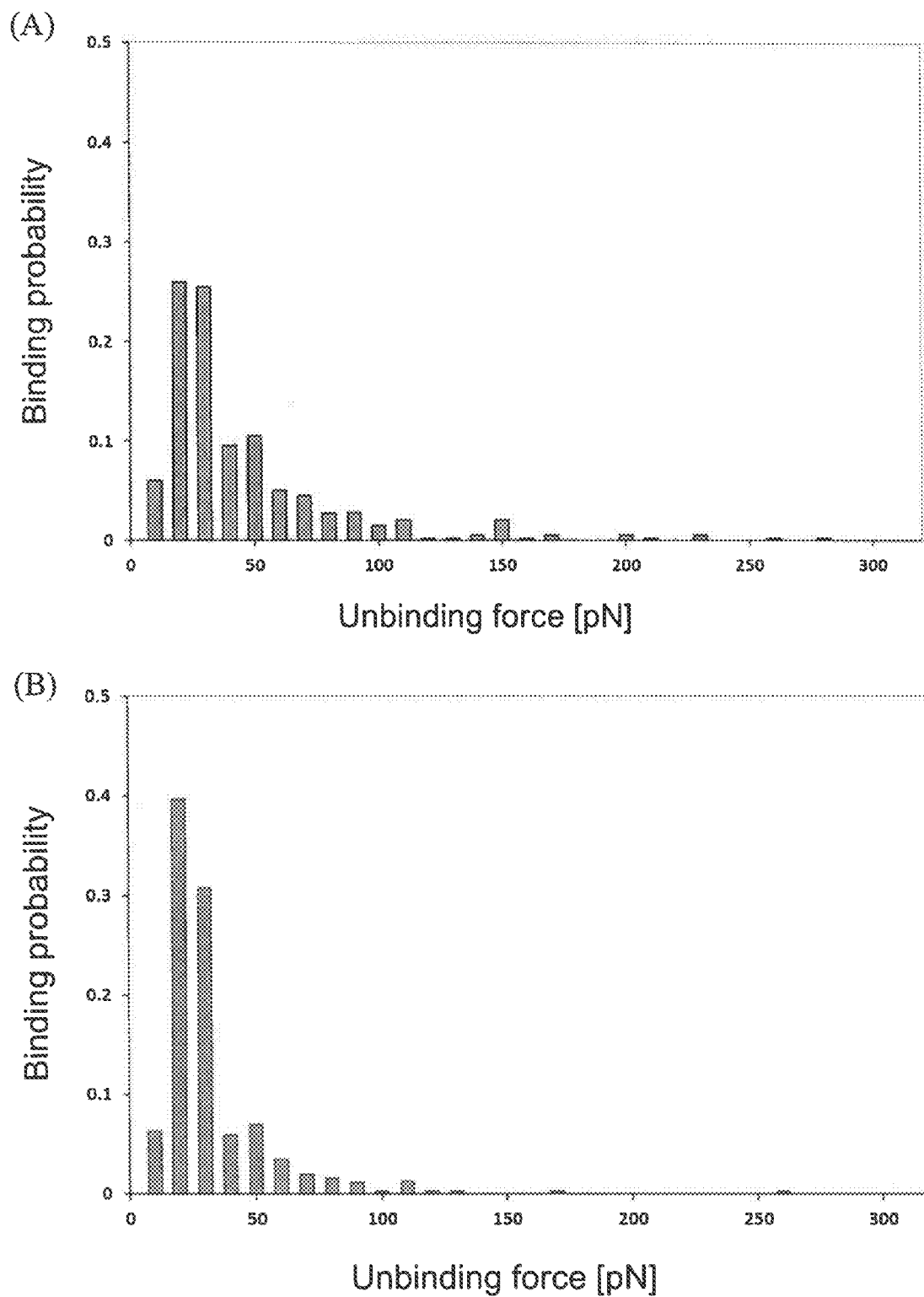
FIG. 7 shows the results of an unbinding force test of Cyn-1324.

Refer to FIG. 7, which shows the results of an unbinding force test of Cyn-1324 while the binding probabilities between CD28 of T-cells and CD80 of B-cells versus the unbinding force are measured in the presence (B) and absence (A) of Cyn-1324. In the absence of Cyn-1324, the average unbinding force is about 41.9 pN. Conversely, in the presence of Cyn-1324, the average unbinding force is reduced to about 29.1 pN. The results shown in FIG. 7 provide the physical evidence that Cyn-1324 repulses the binding between CD28 and CD80, thus blocking the signal 2 pathway induced by the interaction of CD28 and co-stimulatory molecules such as CD80 or CD86.

Figure 8:
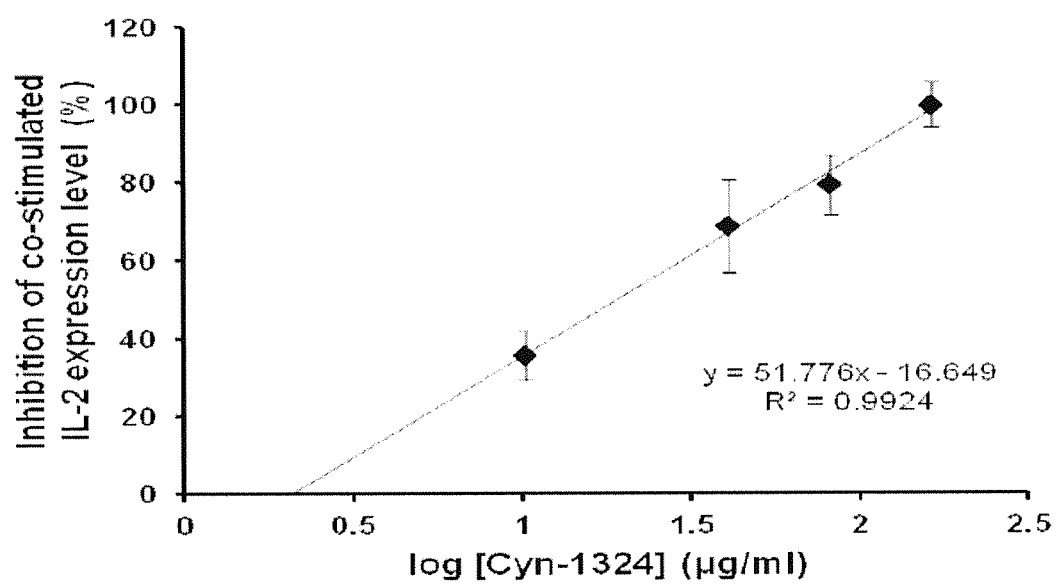
FIG. 8 shows the results of an in vitro IC$_{50}$ measurement of Cyn-1324.

Refer to FIG. 8, which shows the results of in vitro IC50 measurement of Cyn-1324. The $IC_{50}$ represents the dosage which causes 50% reduction of IL-2 expressed from signal 2 pathway of T-cells. As shown in FIG. 8, the IC50 of Cyn-1324 on blocking T-cell immune response is about 20 µg/ml.

Figure 9:
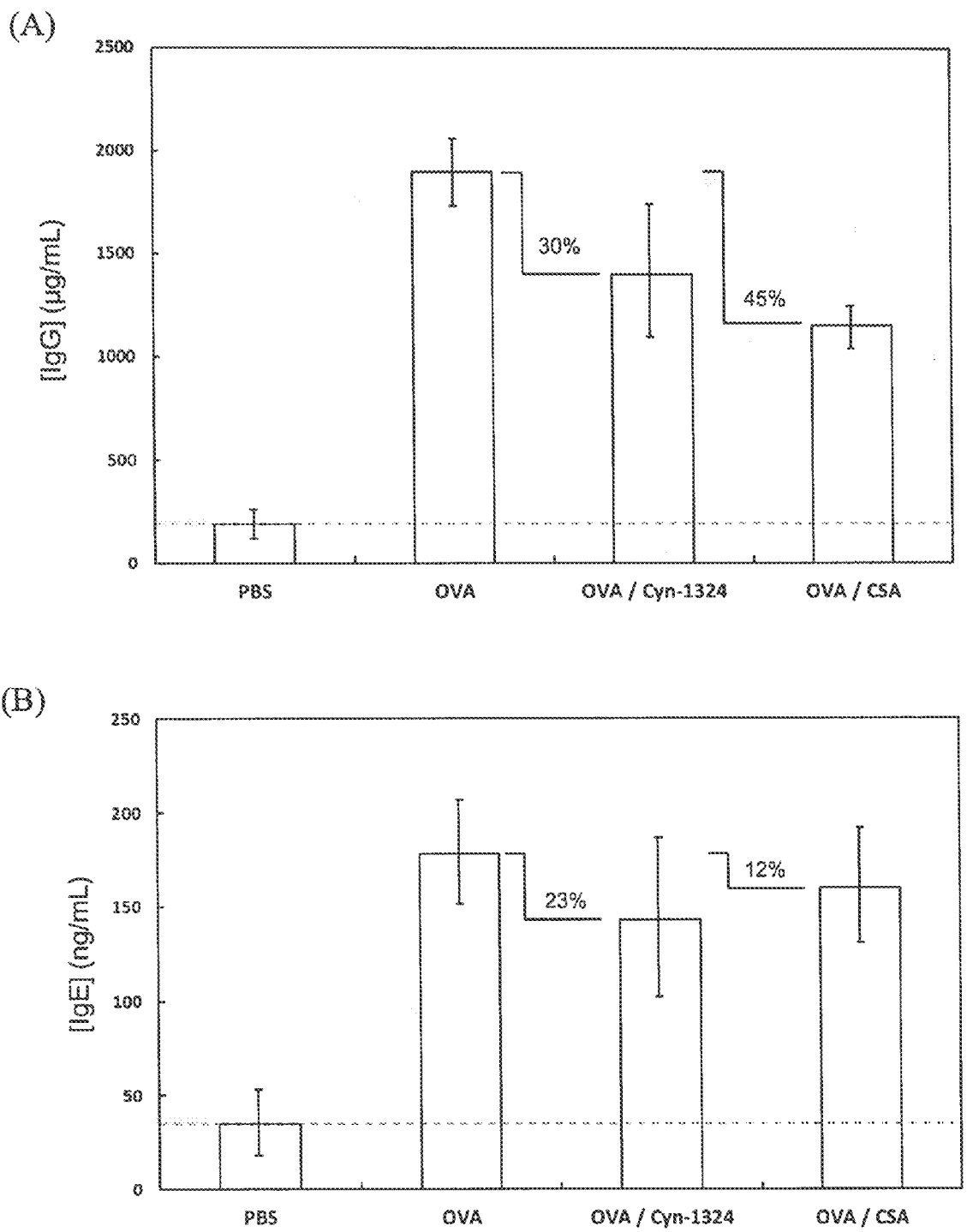
FIG. 9 shows the results of an in vivo animal test of immuno-suppressive effect of Cyn-1324.

Refer to FIG. 9, which shows the results of in vivo animal tests of immuno-suppressive effect of Cyn-1324. The four BALB/c mice groups are treated with phosphate-buffered saline (PBS), ovalbulmin (OVA), OVA/Cyn-1324 or OVA/cyclosporin A (CSA), respectively. CSA is used currently in clinics for suppressing immune response. The 14th-day from the treatments, the serum is collected, and the antibodies such as IgG and IgE are analyzed via ELISA. As shown in FIG. 9, IgG decreases about 30% while IgE decreases about 23% when OVA-sensitized mice are also treated with Cyn-1324. Otherwise, the result of the OVA/CSA group shows that IgG decreases about 45% while IgE decreases about 12%. Accordingly, Cyn-1324 is effective for suppressing immune response.

Figure 10:
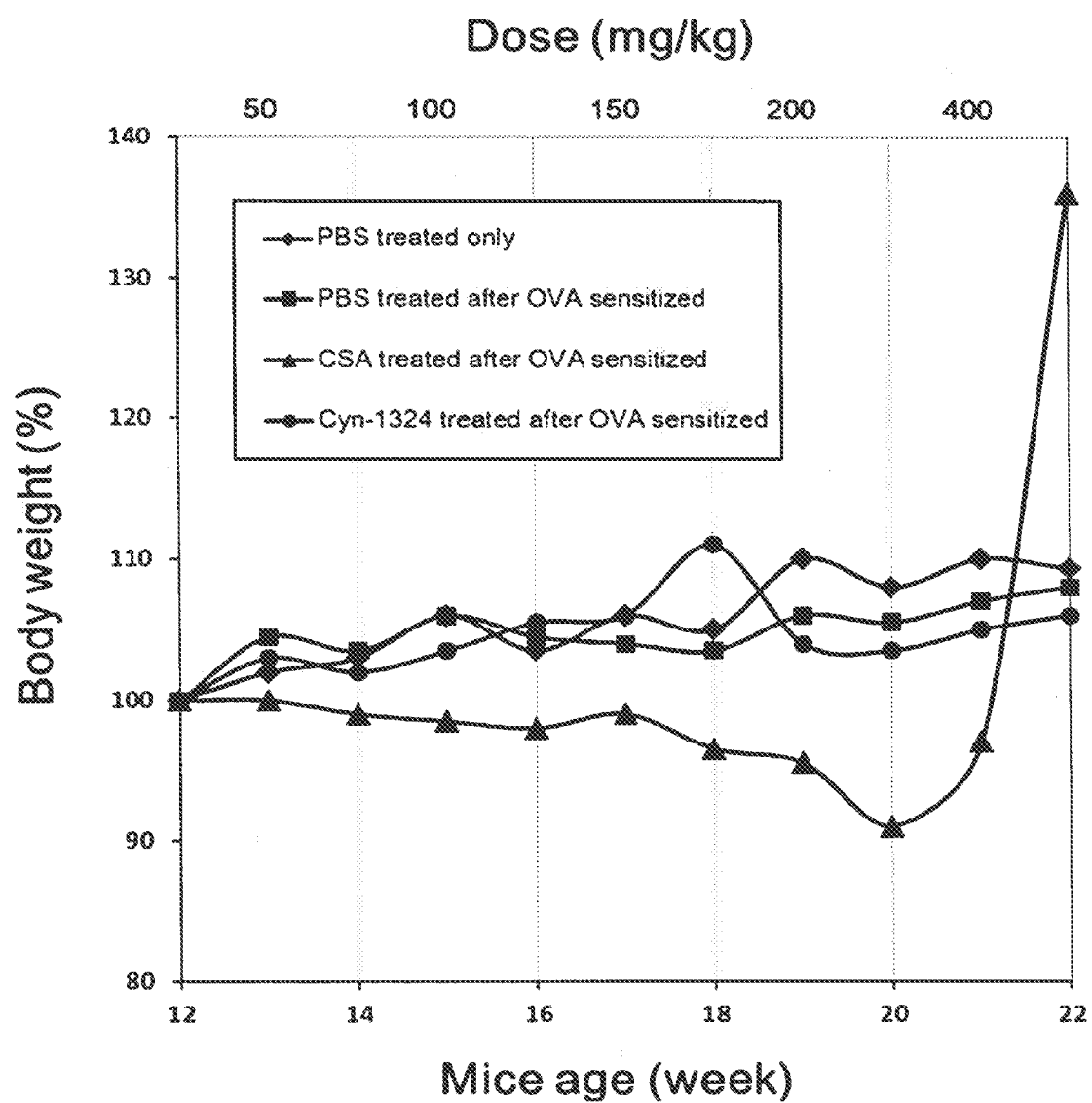
FIG. 10 shows the results of an evaluation of side effect of Cyn-1324.

Refer to FIG. 10, which shows the evaluation of side effect of Cyn-1324 while the body weight variations of mice versus time are shown. One of the four mice groups is treated with PBS, and three of the four groups are sensitized with OVA. The three groups are treaded with PBS, Cyn-1324 or CSA after OVA-sensitization. The results show that the body weight of the CSA group gradually decreased from week-12 to week-20 and suddenly increased until week-22, while body weights of the rest of groups are steadily increased as function of time. Thus, the side effect of Cyn-1324 may be milder than CSA.

Figure 11:
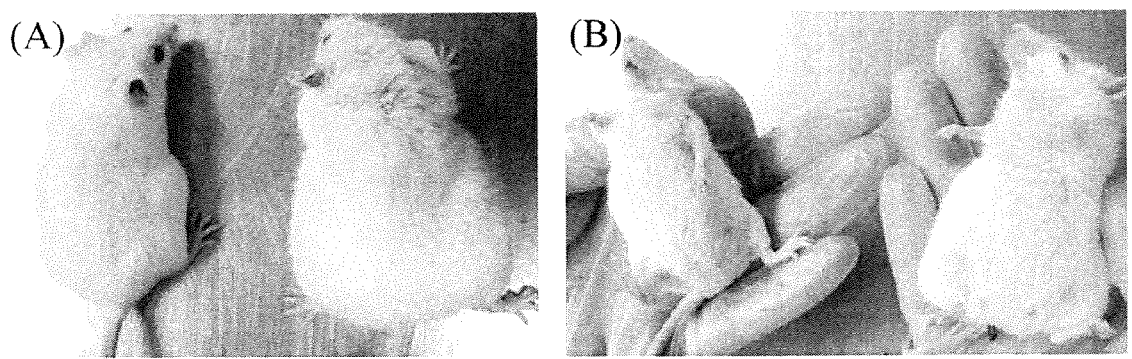
FIG. 11 shows the results of another evaluation of side effect of Cyn-1324.

Refer to FIG. 11, which shows another evaluation of side effect of Cyn-1324 by dorsal (A) and abdominal (B) observations of OVA-sensitized mice from the Cyn-1324 group (left) and the CSA group (right). The results show that the side effect of CSA treatment causes mices' body swollen, while Cyn-1324 does not cause the similar side effect. Otherwise, single dose toxicity test shows that the maximum tolerance dose (MTD) of Cyn-1324 on mice is about 400 mg/kg.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

The invention claimed is:

1. A quinic acid derivative, comprising a quinic acid-like structure for binding to CD28, wherein the quinic acid derivative is:

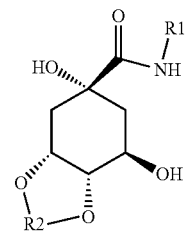

wherein R1 is an organic functional group, which is selected from —CH$_2$CH$_2$Ph, —CH$_2$CH$_2$CH(CH$_3$)$_2$, —CH$_2$(CH$_2$)$_2$OCH$_3$, —CH$_2$CH(CH$_3$)$_2$,

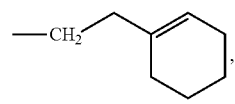,

—CH$_2$CH$_2$CH(Ph)$_2$, cyclopentyl,

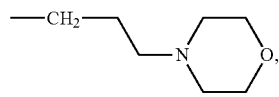, n-pentyl,

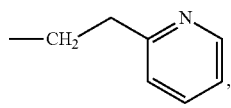

—CH$_2$(CH$_2$)$_2$Ph, or

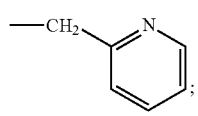

and R2 is a hydroxyl-protecting group.

2. The quinic acid derivative as claimed in claim 1, wherein the quinic acid derivative is use to treat an autoimmune disease, an allergy, transplant rejection or other related immune disorder.

3. The quinic acid derivative as claimed in claim 1, wherein R2 is selected from

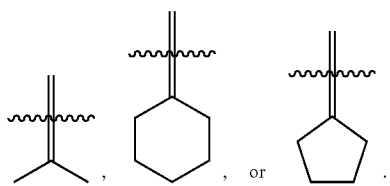

4. A quinic acid derivative:

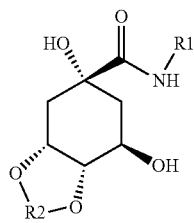

wherein R1 is an organic functional group, and R1 is selected from —CH2CH2Ph, —CH2CH2CH(CH3)2, —CH2(CH2)2OCH3, —CH$_2$CH(CH$_3$)$_2$,

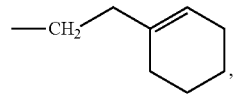

—CH$_2$CH$_2$CH(Ph)$_2$, cyclopentyl,

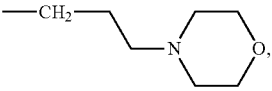

n-pentyl,

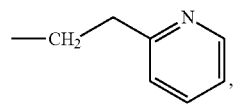

—CH$_2$(CH$_2$)$_2$Ph, or

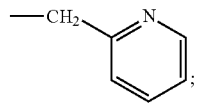

R2 is a hydroxyl-protecting group.

5. The quinic acid derivative as claimed in claim 4, wherein R2 is selected from

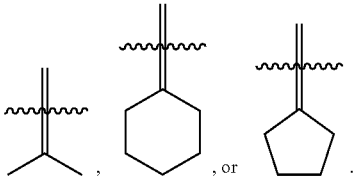

* * * * *